United States Patent [19]
Liu et al.

[11] Patent Number: 5,972,385
[45] Date of Patent: Oct. 26, 1999

[54] COLLAGEN-POLYSACCHARIDE MATRIX FOR BONE AND CARTILAGE REPAIR

[75] Inventors: LinShu Liu, Sunnyvale; Robert Spiro, Half Moon Bay, both of Calif.

[73] Assignee: Orquest, Inc., Mountain View, Calif.

[21] Appl. No.: 09/007,731

[22] Filed: Jan. 15, 1998

Related U.S. Application Data

[63] Continuation-in-part of application No. 08/783,650, Jan. 15, 1997, Pat. No. 5,866,165.

[51] Int. Cl.$^6$ .......................... A61K 38/39; A61K 9/10; A61K 47/42; A61K 47/36
[52] U.S. Cl. ..................... 424/486; 424/78.3; 525/54.1; 525/54.2; 527/205; 530/402; 530/411
[58] Field of Search .................................... 424/484, 486, 424/78.17, 78.26, 78.3; 514/773, 777, 8; 525/54.2, 54.1; 527/205; 530/345, 402, 356, 410–11, 813

[56] References Cited

U.S. PATENT DOCUMENTS 4,517,295   5/1985   Bracke et al. ........................... 435/101

*Primary Examiner*—Edward J. Webman
*Attorney, Agent, or Firm*—Fish & Richardson P.C.

[57] ABSTRACT

A matrix and a method for preparing it are provided to support the growth of tissue, such as bone, cartilage or soft tissue. A polysaccharide is reacted with an oxidizing agent to open sugar rings on the polysaccharide to form aldehyde groups. The aldehyde groups are reacted to form covalent linkages to collagen.

24 Claims, No Drawings

COLLAGEN-POLYSACCHARIDE MATRIX FOR BONE AND CARTILAGE REPAIR

This is a continuation-in-part of U.S. application Ser. No. 08/783,650, filed Jan. 15, 1997, now U.S. Pat. No. 5,866,165.

FIELD OF THE INVENTION

The present invention is directed to crosslinked collagen-polysaccharide matrices for the therapeutic repair of tissue, such as, bone, cartilage and soft tissue; methods of producing such matrices; and methods of using the matrices to repair tissue. The present invention provides a crosslinked collagen-polysaccharide matrix that is administered alone or in combination with other therapeutics, such as growth factors, for tissue repair. The present invention also provides a crosslinked collagen-polysaccharide matrix further comprising fibrin.

BACKGROUND OF THE INVENTION

There is a clinical demand for a bone grafting matrix that offers osteoconductive properties equal to autogenous bone and that can be produced in unlimited supply. Although some bone substitutes are available, many consist of materials that have poor physical handling and resorption characteristics that complicate their use and radiographic evaluation.

Similarly, there is no consistently effective commercial product that supports the maintenance of the chondrocyte phenotype of cartilage tissue, despite years of extensive research. Prior strategies to facilitate the repair of damaged cartilage have included the transplantation of existing host cartilage and/or the implantation of prosthetic devices. Limitations of these methods are the availability of donor tissue and the limited lifespan of prosthetic implants. More recently, the ex vivo cultivation of mature chondrocytes on polymeric scaffolds has been used in an attempt to generate cartilage graft material but this has not yet been widely accepted in part because it involves two surgical procedures: one to harvest chondrocytes and the second to implant them after expansion in vitro.

Collagens and glycosaminoglycans are two classes of biomaterials suited for use in bone regeneration. Collagen based matrices have been used in bone grafting. Type I collagen has good cell adhesive properties, in particular, for bone forming osteoblast cells. Collagen has the capacity to serve both as an active or inert scaffold material for growth.

Hyaluronic acid is a natural component of the cartilage extracellular matrix, and it is readily sterilized, is biodegradable and can be produced in a wide range of consistencies and formats. It is generally biocompatable and its resorption characteristics can be controlled by the manipulation of monomers to polymer forms, most commonly through the esterification of the carboxylic groups of the glucuronic acid residues.

Dextran sulfate is a glycosaminoglycan-like polyionic derivative of dextran and has been shown to be useful as a biomaterial and drug for treatment of hyperlipidemia. It is produced by esterification of dextran, a hydrophilic polymer of glucose synthesized by certain strains of bacteria.

Biological glue comprising fibrin has a long history as a tissue adhesive medical device and is believed to be commercially available in Europe (U.S. Pat. No. 5,260,420, issued Nov. 9, 1993). One obstacle that limits its application is the short turn over and residence time which ranges from a few days to a few weeks depending on the site of implantation. The incorporation of collagen fibers into fibrin glue has been reported (Sierra et al., 1993, Trans. Soc. Biomater., vol. 16:257 and U.S. Pat. No. 5,290,552). However, longer coagulation times are required for the collagen/fibrin compositions compared to fibrin alone.

While these materials have been used separately or in combination with other materials, there has been to date no recognition of combinations and methods of making combinations of such materials to form an advantageous matrix for bone, cartilage, and/or soft tissue repair which does not utilize extraneous cross-linking or ionic binding agents. There remains a need for biodegradable, biocompatible matrices which maintain structural integrity and which can be used to repair tissues without resorting to undesirable ex vivo cultivation methods.

SUMMARY OF THE INVENTION

The present invention provides crosslinked collagen-polysaccharide matrices, methods for preparing such matrices, and methods of using the matrices in the repair of tissue, such as, bone, cartilage and soft tissue. The collagen may be purified, native or modified collagen of any type. In one embodiment, the collagen is Type I collagen and in another embodiment, the collagen is Type II collagen.

The type of polysaccharides which can be used include hyaluronic acid, chondroitin sulfate, dermatan sulfate, keratan sulfate, heparan, heparan sulfate, dextran, dextran sulfate, alginate, and other long chain polysaccharides. In a preferred embodiment, the polysaccharide is hyaluronic acid.

A crosslinked collagen-polysaccharide matrix of the present invention may be used alone to conduct the growth of tissue; in combination with a growth factor to induce the growth of tissue; in combination with fibrin to anchor the matrix into sites of tissue defect, or in combination with both growth factor and fibrin.

Growth factors which can be used with a matrix of the present invention include, but are not limited to, members of the TGF-β superfamily, including TGF-β1,2 and 3, the bone morphogenetic proteins (BMP's), the growth differentiation factors(GDF's), and ADMP-1; members of the fibroblast growth factor family, including acidic and basic fibroblast growth factor (FGF-1 and -2); members of the hedgehog family of proteins, including indian, sonic and desert hedgehog; members of the insulin-like growth factor (IGF) family, including IGF-I and -II; members of the platelet-derived growth factor (PDGF) family, including PDGF-AB, PDGF-BB and PDGF-AA; members of the interleukin (IL) family, including IL-1 thru -6; and members of the colony-stimulating factor (CSF) family, including CSF-1, G-CSF, and GM-CSF.

The method of making a collagen-polysaccharide matrix of the present invention comprises the steps of oxidizing an exogenous polysaccharide to form a modified exogenous polysaccharide having aldehyde groups, and reacting the modified exogenous polysaccharide with collagen under conditions such that the aldehyde groups covalently react with collagen to form a crosslinked matrix. The method may further comprise the step of adding a growth factor to the matrix. A growth factor can be added before or after the step of reacting the modified polysaccharide with the collagen.

The fibrin used in a crosslinked collagen-polysaccharide matrix of the present invention is prepared by contacting a preformed matrix with a source of fibrinogen and thrombin or by combining the fibrinogen and thrombin with the modified exogenous polysaccharide and collagen at the time of reaction. Alternately, fibrinogen and thrombin in a collagen polysaccharide matrix may be added to another preformed collagen polysaccharide matrix. Therefore, the present invention also comprises a method for preparing a crosslinked collagen-polysaccharide matrix comprising fibrin.

The present invention provides methods of using a crosslinked collagen-polysaccharide matrix to conduct the growth of tissue by administering the matrix at the sites of desired tissue repair. The matrix in combination with a growth factor may be administered to induce the growth of tissue at sites of desired repair. A matrix further comprising fibrin may be administered to anchor the matrix into desired sites, such as, tissue defect sites.

As used in this discussion, "repair" is defined as growth of new tissue. The new tissue may or may not be phenotypically or genotypically identical to the original lost tissue. As used herein, "regeneration of tissue" means that the new tissue grown is identical to the lost tissue. Tissue repair can also be the result of replacing lost tissue with non-identical tissues, e.g., for example, the replacement of hyaline articular cartilage with fibrocartilage in a joint defect. The basic cellular properties involved in repair include adhesion, proliferation, migration and differentiation.

By "conduction", it is meant that the host tissue, e.g., bone, cartilage or soft tissue grows by extension of existing tissue onto or into the crosslinked collagen-polysaccharide matrix. In conduction, repair cells move onto and into the matrix to synthesize and remodel new tissue identical to the surrounding host tissue. By induction, it is meant that the growth and differentiation of progenitor repair cells is stimulated. These progenitor cells go on to synthesize and remodel new tissue to be continuous with the surrounding host tissue.

As used herein, a tissue defect can be the result of a congenital condition, trauma, surgery, cancer or other disease.

As used in this discussion, an exogenous polysaccharide refers to a free polysaccharide.

The ratios of the collagen to polysaccharide can be varied to change both the physical and biological properties of the matrix. A higher proportion of collagen will result in a more porous sponge-like matrix. A higher proportion of polysaccharide will result in a more gel-like matrix.

DESCRIPTION OF THE PREFERRED EMBODIMENTS

The method of preparing a matrix of the present invention comprises the steps of opening sugar rings on an exogenous polysaccharide and oxidizing terminal hydroxy groups to aldehydes using, for example, sodium or potassium periodate as a selective oxidizing agent. The amount of aldehyde groups produced in this manner can be stoichiometrically controlled. Typically, from about 1% to 50% of the rings can be opened in this manner. More preferably about 1% to 5% of the rings are opened to form the aldehyde groups. These aldehyde groups can form covalent crosslinks with the collagen at amine sites on the collagen peptide chains. Since the aldehyde groups are formed in situ without the addition of a separate cross-linking compound, the intermolecular distance between the backbone of the polysaccharide chain and the collagen chain which is crosslinked to it is believed to be less than the corresponding distance using a crosslinking compound. Accordingly, the polysaccharide and collagen backbones are relatively closely bound, which produces an advantageous structure for the purpose of providing a matrix that supports, conducts or induces the growth of bone, cartilage or soft tissue.

The starting material for producing the collagen may be purified, native collagen or modified collagen of any type. A preferred collagen for bone growth is Type I collagen, whereas a preferred collagen for cartilage growth is Type II collagen. The collagen may be crosslinked or non-crosslinked, but it is preferred that the collagen be non-crosslinked to provide more accessibility to side groups for crosslinking to the polysaccharide aldehyde groups. If Type I collagen is used for tissue repair where it is desired to mask the inherent cell adhesion site, such as cartilage repair, the adhesion sites can be masked by the use of non cell-adhesive polysaccharides to support the increased cell-to-cell interaction and adhesion.

The type of polysaccharides which may be utilized include hyaluronic acid, chondroitin sulfate, dermatan, dextran sulfate, alginate, and other long chain polysaccharides. Typically, the polysaccharide will have an average molecular weight of about 1,000 to 10,000,000 DA.

The reagents for opening sugar rings on the exogenous polysaccharide may be any selective oxidizing agent which oxidizes a terminal hydroxyl group to an aldehyde, such as potassium or sodium periodate. Other reagents include specific sugar oxidases.

The preferred polysaccharide is hyaluronic acid. The relative proportion of polysaccharide to collagen will impart various physical and biological characteristics to the matrix. The proportion of polysaccharide to collagen may be characterized on a molar ratio basis or on a weight ratio basis. Typically, the ratio by weight of collagen to polysaccharide is from 99:1 to about 1:99. This represents an approximate molar ratio of 99.9:0.1 to 1:9, respectively, assuming an average molecular weight of 1,000,000 daltons for hyaluronic acid and 100,000 daltons for collagen. The molar ratio may vary depending on the actual molecular weight of the polysaccharide and collagen used. In a preferred embodiment disclosed herein, the ratio by weight of collagen to polysaccharide is from 9:1 to about 1:9.

The ratios of the collagen to polysaccharide can be varied to change both the physical and biological properties of the matrix. Biologically, a higher proportion of Type I collagen will more closely mimic the composition and architecture of bone, whereas a higher proportion of Type II collagen will more closely mimic the composition of cartilage. Bone forming cells will interact with specific cell adhesion sites on collagen and will divide, migrate and differentiate to form new bone.

Alternatively, increasing the proportion of polysaccharide, preferably hyaluronic acid, will more closely mimic a natural cartilage matrix. In addition, a higher proportion of polysaccharide will mask some specific cell adhesive sites on collagen and will favor other cell—cell interactions and aggregation important in the development of cartilage tissue.

Growth factors which can be used with a matrix of the present invention include, but are not limited to, members of the TGF-β superfamily, including TGF-β1,2 and 3, the bone morphogenetic proteins (BMP's), the growth differentiation factors(GDF's), and ADMP-1; members of the fibroblast growth factor family, including acidic and basic fibroblast growth factor (FGF-1 and -2); members of the hedgehog family of proteins, including indian, sonic and desert hedgehog; members of the insulin-like growth factor (IGF) family, including IGF-I and -II; members of the platelet-derived growth factor (PDGF) family, including PDGF-AP, PDGF-BB and PDGF-AA; members of the interleukin (IL) family, including IL-1 thru -6; and members of the colony-stimulating factor (CSF) family, including CSF-1, G-CSF, and GM-CSF. Growth factor preparations are obtained either commercially or isolated and purified from tissue or from recombinant sources. Growth factors can be loaded into the collagen/HA/fibrin matrices across a wide dose range (fentogram to millgram range). Factors such as cost, safety and the desired growth factor release profile will dictate the amount of growth factor that is loaded onto the matrix.

Thrombin acts as a catalyst for fibrinogen to provide fibrin. In the present invention, thrombin is added to fibrinogen in an amount sufficient to catalyze polymerization of the fibrinogen being used. In one embodiment, the fibrinogen and thrombin are first combined and then quickly added to a preformed crosslinked collagen-polysaccharide matrix, which can also then be added to another preformed collagen-polysaccharide matrix. In another embodiment of the present invention, the fibrinogen and thrombin are added individually to a reaction containing oxidized exogenous polysaccharide and collagen. In this embodiment, it is desired to keep the fibrinogen and thrombin separated and the oxidized, exogenous polysaccharide and collagen separated until final reaction is desired.

The concentration of fibrinogen used in forming the matrix is preferably 10 mg/ml or greater. The thrombin is added to the fibrinogen in a concentration of from about 0.01 NIH units to about 100 NIH units/ml and preferably from about 0.1–2.0 NIH units/ml. The thrombin is commercially available from a variety of sources including from Calbiochem-Novabiochem, San Diego, Calif. Fibrinogen may be derived from autologous patient plasma or from commercial sources, such as Calbiochem-Novabiochem, San Diego, Calif.

The matrices according to the present invention may be formed into any shape by lyophilization, or wet-laying and air drying in molds of the desired shape. The lyophilized or wet-layed material having a high proportion polysaccharides may also be formed into viscous gels for injection or direct application into a fracture.

The usefulness of the matrices according to the present invention can be shown by both in vitro and in vivo tests. For the in vitro tests, primary fetal rat calvarial cells, harvested by a series of collagenase digestions, according to the method of Wong and Cohn (*PNAS USA* 72:3167–3171, 1975), or primary rat epiphyseal cartilage Thyberg and Moskalewski, (*Cell Tissue Res.* 204:77–94, 1979) or rabbit articular chondrocytes, harvested by the method of Blein-Sella O. et al., (*Methods Mol. Biol.*, 43:169–175, 1995), are seeded into the matrices and cultured under conventional conditions for 1–4 weeks. Cultures are then processed and evaluated histologically.

The chondroconductive capability of the matrices of the present invention can be determined by successful support of adhesion, migration, proliferation and differentiation of primary rat bone marrow and stromal cells as well as retinoic acid-treated primary rat or rabbit chondrocytes. Bone marrow and bone marrow stromal cells closely approximate the early chondroprogenitor cells found in the subchondral bone marrow of full-thickness defects. Bone marrow are harvested from the long bones of 2–3 week-old inbred Lewis rats and added directly to a matrix and cultured for 2 weeks under standard conditions. The adherent stromal cell population that grows out of these cultures are passaged and frozen for use. Cells from up to six passages are used for culturing or seeding on the matrix.

Retinoic acid-treated chondrocytes represent the latter stages of chondrogenesis. Retinoic acid treatment of primary is performed prior to culturing or seeding the cells on a candidate matrix (Dietz, U. et al., 1993, *J. Cell Biol.* 52(1): 57–68).

In an alternative method, in vitro studies of the early and late stage chondrocytes are merged to allow stromal cells to condition the matrices and then to replace them with more mature chondrocytes. In this way, evolution of the matrices during the early phases of chondrogenesis may be tested for effects on the later stages of the process.

Cell adhesion and proliferation on the matrix are monitored using an MTS assay that can measure cell number and viability based on mitochondrial activity. Stromal cells or chondrocytes are cultured on matrices for 6–18 hrs. in the presence or absence of serum for adhesion analysis and for 1–2 weeks for proliferation assessment.

For cell migration testing, matrices are coated or fitted onto porous Trans-well membrane culture inserts (Corning). Stromal cells are seeded on top of the matrices in the upper chamber of the Trans-well and a chemoattractant (growth factor, PDGF) placed in the bottom chamber. After 12–18 hrs of culture the cells that have migrated through the matrix to the bottom side of the Trans-well membrane are quantitated by the MTS assay. Matrices are removed from the upper chamber and processed histologically to assess degree of infiltration.

The analysis of differentiation markers relevant to chondrogenesis and osteogenesis are evaluated at both the protein and transcriptional level. The specific markers that may be analyzed include: 1) Type II collagen and IIA, IIB isoforms; 2) Aggrecan proteoglycan; 3) Type IX, X and XI collagen; 4) Type I collagen; 5) Cartilage matrix protein (CMP); 6) Cart-1 transcription factor; 7) Fibronectin (EDA, EDB isoforms); 8) Decorin proteoglycan; 9) Link protein; 10) NG-2 proteoglycan; 11) Biglycan proteoglycan; 12) Alkaline phosphatase. Differentiation may be measured by Northern/PCR analysis, Western blotting or by metabolic cell labeling.

For Northern/PCR analysis, RNA are isolated by standard procedures from stromal cells or chondrocytes that have been cultured on composite matrices. Time course tests may be used to determine optimal culture periods that range from 1 to 6 weeks depending on the cell type. The isolated RNA is analyzed by Northern gel and hybridization techniques with specific cDNA or PCR amplified probes. Northern analysis is quantified by densitometric scanning of autoradiographs and normalization to housekeeping gene signals (G3PDH). Northern analysis may be supplemented with quantitative PCR analysis using primers generated from the published cDNA sequences of the genes to be analyzed.

For Western blotting, solubilized protein lysates are isolated from cells cultured on composite matrices by standard techniques (Spiro R. C., et al., 1991, *J. Cell. Biol.*, 115:1463–1473). After the lysis of cells the matrices are extracted in stronger denaturants (8 M urea, GnHCL) to remove and examine matrix-bound or incorporated proteins. Protein samples are analyzed by standard Western blotting techniques using specific polyclonal or monoclonal antibodies.

For metabolic cell labeling, cells cultured on a composite matrix are metabolically radiolabeled with $^{35}SO_4$, $^{35}S$-methionine or $^3H/^{14}C$-labeled amino acids by standard techniques (Spiro et al., supra). Solubilized cellular and matrix-associated proteins are quantitatively immunoprecipitated with antibodies specific for the protein of interest and analyzed by SDS-PAGE (Spiro et al., supra). Quantitation of results are performed by densitometric scanning of autoradiographs and signals will be normalized to either cell equivalents or to a house-keeping protein such as actin.

Additionally, the ability of a matrix of the present invention to support chondrogeneic differentiation in vivo may be tested in an inbred rat soft tissue implant model. Rat bone marrow or stromal cells described above are seeded onto matrices at high density, cultured overnight in MEM medium containing 10% FBS serum and antibiotics, then transferred into Millipore diffusion chambers and implanted intraperitoneally or subcutaneously into 8 week-old recipients. Chambers are harvested after 3 weeks and evaluated histologically for cartilage formation.

A transplantation model in outbred rats is used to evaluate the ability of the composite matrices to maintain the cartilage phenotype in vivo. Rib costal cartilage chondrocytes are seeded onto matrices at high density and cultured overnight in Ham's F-12 containing 1% rat serum and antibiotics. The seeded matrices are then implanted into posterior tibial muscle pouches created by blunt dissection in 8 week-old male Sprague-Dawley rats. Explants are taken at 14 and 28 days and evaluated histologically for matrix compatibility, cartilage growth, and maintenance of the differentiated phenotype based on staining for aggrecan and type II collagen.

In addition, the ability of a matrix of the present invention to interact with extracellular matrix proteins (proteoglycans, proteins and growth factors) found in the surrounding serum, tissue fluid, or in the secretion products of chondroprogenitor cells correlate with the chondroconductive potential of a matrix. The interaction of the matrices of the present invention with extracellular matrix proteins may be measured by means known to those of skill in the art such as, Western blotting, affinity co-electrophoresis techniques and binding characteristics.

To assay serum protein binding to a matrix of the present invention, the matrix is incubated in culture media containing increasing amounts of serum (various species and sources). After washing, bound proteins are eluted by boiling in SDS-PAGE sample buffer and unsolubilized matrix will be removed by centrifugation. SDS-PAGE analysis is used to initially document the binding pattern of the matrices. Western blotting is then performed to identify specifically bound components such as fibronectin and vitronectin.

Affinity coelectrophoresis is used to analyze proteoglycan binding to a matrix of the present invention. $^{35}SO_4$-labeled or iodinated proteoglycan (aggrecan) isolated from bovine and rat (or other sources) is loaded into ACE gels (Lee, M. K. et al., 1991, 88:2768–2772) containing composite matrices or collagen scaffolds alone. The binding affinity of aggrecan for collagen scaffolds plus and minus hyaluronic acid or dextran sulfate are taken as a measure of the ability of composite matrices to organize a cartilage matrix.

An evaluation of protein interactions with collagen-based composite matrices can potentially be hindered by the large excess of collagen protein. The collagen scaffolds have enough inherent structural integrity and are crosslinked to an extent that will prevent their complete solubilization, but some collagen protein may become solubilized in the SDS-PAGE sample buffer. Thus, this could obscure the visualization of other bound proteins, particularly the cell-synthesized collagens, and may also cause high background in Western blot analysis. Therefore, an alternative approach is to use radiolabeled or biotinylated proteins for the binding analysis. Serum proteins may be biotinylated prior to incubation with the composite matrices and then developed with avidin-based reagents. Both approaches allow the visualization of matrix-associated components without the interference of the scaffold collagen protein.

Alternatively, the shift in expression from Type I to Type II collagen and the splicing of the Type II collagen transcript from the Type IIA to the Type IIB isoform (Sandell, L. J. et al., 1991, *J. Cell Biol.* 114:1307–1319) are measured by means known to those of skill in the art to determine differentiation down a chondrogenic pathway. Also, the expression of the cartilage-associated proteoglycan, aggrecan (Schmid, T. M., et al., 1985, *J. Cell Biol.* 100:598–605 and Kuettner K. E. 1992, *Clin. Biochem.* 25:155–163) and a cartilage homeoprotein transcription factor (Cart-1) appear to be markers for cells committed to the chrondrocytic lineage.

For the in vivo tests, the matrices are evaluated for the capabilities for supporting osseous healing in a rat cranial defect model by implantation into a 5 mm by 3 mm defect created in the parietal bone of 6 weeks old male Sprague-Dawley rats. The defects are evaluated at 28 days by radiographic and histologic analysis.

The in vivo model for cartilage repair is a full-thickness articular cartilage defect in the rabbit (Amiel et al., 1985, *J. Bone Joint Surg.* 67A:911). Defects measuring approximately 3.7 mm in diameter and 5 mm deep defect are created in the center of the medial femoral condyles of adult male New Zealand white rabbits. The defects are then either filled with matrix or left unfilled as controls. The defects are evaluated morphologically and histologically at 6 and 12 weeks.

The matrices of the present invention may be used for the treatment of bone and/or cartilage defects associated with surgical resection, such as spinal fusions; trauma; disease; infection; cancer or genetic defects. The matrices according to the present invention may be administered through implantation, direct application or injection depending on the intended application of the matrix, the physical properties of the matrix and the ratio by weight of collagen to polysaccharide in the matrix.

In one aspect of the present invention, the matrix is provided having a higher proportion of collagen compared to polysaccharide, is in a sponge-like form and is surgically implanted at a site where growth of new bone tissue is desired, such as in spinal fusions. In one aspect, the matrix further comprises a growth factor, such as BMP-2. In another aspect, the matrix further comprises fibrin to facilitate anchoring of the matrix into the desired site. In another aspect of the present invention, the matrix has a higher proportion of polysaccharide compared to collagen, is formed into a viscous gel and is either directly applied or injected into a site where growth of new bone tissue is desired, such as in filling bone defects, fracture repair and grafting periodontal defects. In yet another aspect of the present invention, the matrix is provided with a higher proportion of polysaccharide, is formed into a viscous gel and is injected directly or delivered through an arthoscopic procedure into a site where growth of cartilage tissue is desired, such as in injury induced cartilage damage or disease-induced cartilage damage such as in, osteoarthritis or rheumatoid arthritis.

As will be understood by those of skill in the art, the amount of matrix to be administered to conduct growth of bone or cartilage tissue depends upon the extent of the bone or cartilage defect to be treated. As will also be understood by those of skill in the art, the cost, safety, and desired growth factor release profile will dictate the type and amount of growth factor that is loaded onto the matrix.

The following examples are provided for purposes of illustration and are not intended to limit the invention in any way.

EXAMPLE 1

This example illustrates the production of a variety of matrices for use in bone and/or cartilage repair. In the following matrices, Type I collagen was used as a raw material. Semed F collagen (Type I, insoluble) and Semed S collagen (Type I, acid soluble) were from Kensey-Nash. Hyaluronic-polyaldehyde, dextran-polyaldehyde, dextran sulfate/polyaldehyde, and chondroitin sulfate/polyaldehyde were prepared by oxidation of the related polysaccharide with reagent grade sodium periodate.

The matrix in this case was based on the reaction of protein amine residues on the collagen with the active aldehyde groups generated on the sugar rings of the polysaccharides. Matrices with various surface properties and biological activity are synthesized by controlling the ratios of the collagen to the polysaccharides, the type of collagen, the types of polysaccharides, as well as the density of the aldehyde groups generated on the polysaccharides.

Semed F collagen (8.1 parts) and Semed S collagen (0.9 part) were dispersed in a hyaluronate/polyaldehyde solution (1 part, 5% of the repeat units were oxidized: pH 3– 3.5) containing 10 mM sodium cyanoborohydride (NaCNBH$_3$) in a heavy duty blender at low speed for 10 seconds followed by high speed for another 5 seconds. The slurry (solids concentration: 28 mg/ml) was poured into a mold, incubated at ambient temperature for 24 hours and lyophilized. This formed a sponge which was washed several times in distilled water to completely remove the NaCNBH$_3$. The washed sponge was then lyophilized.

The above procedure was followed to make other matrices using the starting materials as follows:

| | |
|---|---|
| Semed F collagen (0.9 part) | Hyaluronate/polyaldehyde |
| Semed S collagen (0.1 part) | solution (1 part, 5% of the repeat units oxidized) Solids concentration: 15 mg/ml |
| Semed F collagen (0.9 part) | Hyaluronate/polyaldehyde |
| Semed S collagen (0.1 part) | solution (2 parts, 5% of the repeat units oxidized) Solids concentration: 15 mg/ml |
| Semed F collagen (0.9 part) | Hyaluronate/polyaldehyde |
| Semed S collagen (0.1 part) | solution (4 parts, 5% of the repeat units oxidized) Solids concentration: 15 mg/ml |
| Semed F collagen (0.9 part) | Hyaluronate/polyaldehyde |
| Semed S collagen (0.1 part) | solution (4 parts, 1% of the repeat units oxidized) Solids concentration: 15 mg/ml |
| Collagen Type II (9 parts) | Hyaluronate/polyaldehyde solution (1 part, 5% of the repeat units oxidized) Solids concentration: 15 mg/ml |
| Collagen Type II (1 part) | Hyaluronate/polyaldehyde solution (1 part, 5% of the repeat units oxidized) Solids concentration: 15 mg/ml |
| Semed F collagen (7 parts) | Hyaluronate/polyaldehyde |
| Collagen Type II (2 parts) | solution (1 part, 5% of the repeat units oxidized) Solids concentration: 15 mg/ml |
| Semed F collagen (8.1 parts) | Dextran/polyaldehyde |
| Semed S collagen (0.9 part) | solution (1 part, 5% of the repeat units oxidized) Solids concentration: 28 mg/ml |
| Semed F collagen (8.1 parts) | Dextran sulfate/polyaldehyde |
| Semed S collagen (0.9 part) | (1 part, 5% of the repeat units oxidized) Solids concentration: 28 mg/ml |
| Semed F collagen (8.1 parts) | Chondroitin |
| Semed S collagen (0.9 part) | sulfate/polyaldehyde (1 part, 5% of the repeat units oxidized) Solids concentration: 28 mg/ml |
| Semed F collagen (0.9 part) | Hyaluronate/polyaldehyde |
| Semed S collagen (0.1 part) | solution (4 parts, 5% of the repeat units oxidized) Solids concentration: 15 mg/ml |

EXAMPLE 2

The matrices of Example 1 were evaluated for their capability of supporting osseous healing in a rat cranial defect model. A matrix of the present invention comprising 1 part collagen (Semed F collagen 0.9 part: Semed 0.1 part) to 1 part hyaluronate/polyaldehyde solution (5% of the repeat units oxidized from solids concentration at 15 mg/ml) was implanted into a 5 mm by 3 mm defect created in the parietal bone of 6 weeks odd male Sprague-Dawley rats. The defects were evaluated at 28 days by radiographic and histologic analysis.

The radiographic analysis of the defects suggests that significant bony healing had occurred to unfilled defects. All matrix-filled defects were completely radiodense, with no distinctive defect borders, which indicated complete healing. Unfilled defects appeased as ovoid radiolucent areas with rounded corners, suggesting minimal healing.

The histologic evaluation correlated with radiographic results. The defects were filled with a continuous patch of woven bone that was normal in cellularity and structure, with presumptive marrow spaces and maturing hemopoietic marrow. Traces of residual implant material were shown along with a mild chronic inflammatory infiltrate. In some areas, the new bone was deposited within the interstices of the implant material and bone surfaces were lined with active osteoblasts. These results demonstrate that the implantation of a collagen polysaccharide-polyaldehyde matrix conducted the bone formation of normal repairable bone in this critical defect model.

EXAMPLE 3

This example illustrates the osteoconduction and osteoinduction of CN/HA matrices of the present invention. In one aspect, osteoconduction was examined by implantation of a CN/HA matrix alone in a rat cranial defect, with radiographic and histological evaluation of bone formation after 1, 2, 3, and 4 weeks. In another aspect, osteoinduction was examined by intramuscular implantation of CN/HA matrices containing bone morphogenetic protein (BMP) with subsequent histological and biochemical assessment of ectopic bone formation.

Materials and Methods

Preparation of Matrix with and without BMP

A crosslinked collagen-hyaluronate 9:1 matrix was prepared as described in Example 1 and lyophilized. For preparation of a matrix with growth factor, BMP (obtained from Intermedic Orthopedics, Denver, Colo.) was dissolved and added to the lyophilized matrix to final concentration of 0.1% (50 $\mu$g per 50 $\mu$l of matrix). The matrix/growth factor combination was then lyophilized a second time prior to implantation into the cranial defect.

Osteoconduction in Rat Cranial Defects

To evaluate the ability of a collagen-hyaluronic acid matrix (CN/HA scaffolds) to support the ingrowth of bony tissue, CN/HA scaffolds were implanted in defects created in the parietal bones of 6 week-old male Sprague Dawley rats by a modification of a previously described method (Mulliken, J. B. et al, 1980, reconstru. Surg. 65:553–559). Briefly, bilateral, rectangular defects of approximately 5 mm by 3 mm were made using a low speed Dremel drill fitted with an engraving bit under constant irrigation during drilling. Left defects were filled with one pre-cut dry piece of CN/HA scaffold, and right defects remained unfilled and served as untreated controls. Animals were sacrificed after 7, 14, 21 and 28 days, and calvaria were excised and fixed in 10% neutral buffered formalin.

Intramuscular Ectopic Bone Induction

To evaluate the ability of CN/HA scaffolds to deliver osteoinductive growth factors, implants of CN/HA containing bone morphogenetic protein (BMP) were placed in bilateral pouches created in the tibial muscles of 4 week-old male Sprague-Dawley rats. Each CN/HA matrix was loaded with 50 $\mu$g of BMP by absorption and subsequent lyophilization, and the contralateral limb received implants of CN/HA without BMP. Animals were sacrificed after 21 days, and implant materials were excised from surrounding tissue. Explanted tissues were cut into two pieces: one piece extracted and assayed for alkaline phosphatase (Lowry et al, 1954, J. Biol. Chem. 207:19 and Sampath, et al, 1981, Proc. Natl. Acad. Sci. 78:7599–7603) and the other piece fixed in 10% neutral buffered formalin, decalcified and processed for histological evaluation. Paraffin sections of 6 $\mu$m thickness were stained with hematoxylin and eosin and examined for ectopic bone formation, inflammation, and residual implant appearance. Alkaline phosphatase activity was expressed in units where 1 unit equals nmoles p-nitrophenol produced (from p-nitrophenylphosphate substrate) per minute at 37° C.

Radiographic Evaluation

Radiographs of fixed calvaria taken with a Faxitron X-ray unit (Hewlett-Packard, Model 43855A) were recorded on X-Omat-TL film (Kodak). Tracings of radiolucent areas were quantified to calculate % reduction in defect size relative to untreated defects.

Histological Evaluation

Calvarial and intramuscular implant specimens were decalcified in Formical (American Histology, Lodi, Calif.). Transverse gross cuts were made through the approximate center of the cranial defects prior to processing. Six $\mu$m paraffin sections at the center of the defects or explanted tissues were stained with hematoxylin and eosin. Tissues were evaluated for biocompatibility (inflammation), residual implant persistence and new bone formation. Bony healing of cranial defects were scored subjectively on a linear scale of 1 to 5, based on the width of the defect bridged with reparative bone.

Results

Osteoconduction of CN/HA Matrices

Untreated cranial defects typically demonstrated minimal bony repair during the 4 week period. Radiographs of excised calvaria showed a slight rounding of the unfilled rectangular defects after 28 days, which indicated that some spontaneous bony repair from the cut edges had occurred. Histologically, unfilled defects after 1, 2, 3, and 4 weeks were bridged by a thin band of fibrous tissue, with a small amount of repair by woven bone at the cut ends of the lamellar calvarial bone evident at 2 weeks. The reparative bone was of normal staining and cellular characteristics. Typically, untreated cranial defects were minimally proliferative and exhibited no significant inflammatory response.

In comparison, defects filled with CN/HA matrices showed progressively increasing radioopacity over 4 weeks. By 4 weeks, treated defects were completely or nearly completely radiodense. The % reduction in defect areas for treated defects relative to untreated controls are shown in Table I.

TABLE I

Summary of Radiographic and Histological Evaluation

| Time Point | Radiographic Score (% reduction in defect area) | Histological Bone Score CN/HA Treated (mean ± SD) | Histological Bone Score Untreated (mean ± SD) |
|---|---|---|---|
| 1 week | 20 ± 12% | 2.0 ± 1.5 | 1.0 |
| 2 weeks | 43 ± 36% | 4.0 ± 1.3 | 1.5 ± 0.8 |
| 3 weeks | 69 ± 12% | 4.0 ± 1.5 | 1.2 ± 0.4 |
| 4 weeks | 86 ± 12% | 4.8 ± 0.4 | 1.5 ± 0.5 |

Likewise, histological evaluation showed increasing reparative bone formation during the 4 week period (see Table 1). Minimal reparative bone formation was observed at the cut parietal bone after 1 week. The ingrowth of fibrous tissue was accompanied by a diffuse chronic inflammatory cell infiltrate. In some areas, a condensation of the fibrous tissue had occurred which resembled osteoid deposition. At this early time point, the majority of the defect was filled with the reticular network of the CN/HA matrix material.

At two weeks, variable amounts of new bone formation was observed, with 3 of 6 defects completely or nearly completely bridged by very young new woven bone. The new bone was of normal histological appearance, and appeared to have incorporated implant material into its substance. The first stages of osteoid and bone accretion appeared to be in progress in the central region of the CN/HA matrix within a vascularized fibrous tissue. At this time point, a generally mild chronic inflammatory response was associated with CN/HA matrices.

Similarly, 4 of 6 defects treated with CN/HA were essentially completely bridged by woven bone at 3 weeks, with the remaining 2 specimens exhibiting modest bony repair. The new bone contained osteocytes in lacunae, reversal lines, numerous osteoblast-lined bone surfaces, and maturing marrow spaces. Small amounts of residual matrix material in association with fibrous tissue and a mild chronic inflammatory response were also observed peripherally to the newly formed bone.

By 4 weeks, 5 of 6 defects were completely or almost completely bridged by reparative woven bone. Remodeling and maturation of the woven bone had apparently occurred as lamellar bone and hematopoietic marrow spaces were present within the woven bone. Very mild inflammation consisting of a diffuse chronic inflammatory cell infiltrate was associated with fragments of residual CN/HA matrix and fibrous tissue in a few areas adjacent to the new bone.

Ectopic Bone Formation Induced By BMP Loaded CN/HA Scaffolds

After 21 days, intramuscular implantation of CN/HA supported the ingrowth of a fine fibrous tissue within the interstices of the matrix scaffold and elicited a mild to moderate chronic inflammatory cell response. Implants were surrounded by muscle tissue of histologically normal appearance and a slightly thickened capsule of fine fibrous tissue. A few multinucleate giant cells were also present peripherally in relation to implant material.

In contrast, CN/HA scaffolds loaded with 50 μg BMP induced extensive ectopic bone formation after implantation in rat tibial muscle pouches for 21 days. Islands of new bone had formed throughout the CN/HA matrix within an ingrowth of fibrovascular tissue. The osseous tissue in the central region of the implant appeared less mature than the woven bone present at the periphery of the implant. The interconnecting woven bone spicules contained reversal lines, osteocytes in lacunae and many areas of presumptive hematopoietic marrow. A few scattered chondrocytes were also present within the new bone. Only traces of residual matrix material could be discerned within the bony ossicle. A thickened fibrous tissue capsule containing some chronic inflammatory cells was present peripherally. The specific alkaline phosphatase activity for 21 days explants of CN/HA scaffolds containing 50 μg BMP was 22±6 units, while alkaline phosphatase was not detected (<1 unit) in explants of CN/HA only.

CN/HA matrices (implants) alone were osteoconductive and supported new bone formation when implanted into rat cranial defects. CN/HA implants were composed of a reticular network of collagen fibers with a channeled structure that promoted cellular ingrowth throughout the implant. New bone formation was evident at 2 weeks by radiographic and histological assessments. After 4 weeks, defects were nearly completely filled with new woven bone, in comparison to untreated defects which were typically bridged by a thin band of fibrous tissue with minimal bony repair. Only small amounts of residual CN/HA implant material was present after 4 weeks, the majority of the implant either resorbed or incorporated into the newly formed bone. Matrices demonstrated good biocompatibility and elicited no significant inflammatory response. CN/HA matrices alone served as a scaffold for tissue regeneration, promoting the recruitment of mesenchymal fibrous tissue into the defect and the subsequent deposition of osteoid and bone.

CN/HA matrices implanted intramuscularly in the rat were well-tolerated and promoted the growth of fibrovascular tissue after 21 days. When CN/HA matrices contained 50 μg of BMP, extensive ectopic bone formation was induced. Although new woven bone formation was evident throughout the entire implant, the ossicle appeared to be more mature peripherally. Similar to CN/HA matrix alone implanted in cranial defects, virtually all of the matrix plus BMP had been resorbed or incorporated into the new bone. These results indicate that CN/HA matrices are suitable delivery vehicles for osteoinductive factors and support the cascade of events which occur as mesenchymal cells differentiate into bone. The efficiency of CN/HA matrices in delivery of osteoinductive factors, can be ascertained by an in vivo BMP dose-response study.

EXAMPLE 4

This example illustrates that a matrix of the present invention will support the maintenance of chondrocyte phenotype in vitro.

Primary rat chondrocytes made by the method of Blein-Sella O. et al., supra, were seeded into a matrix made by the method disclosed in Example 1 comprising 1 part collagen (Semed F collagen 0.9 part: Semed 0.1 part) to 1 part hyaluronate/polyaldehyde solution (5% of the repeat units oxidized from solids concentration at 15 mg/ml) and cultured under conventional conditions for 1–4 weeks. Cultures were then processed and evaluated histologically. The results show that calvarial cells seed on the matrix grow and continue to express alkaline phosphatase, a marker for bone-forming cells. Chondrocytes seeded on the matrix also proliferate and synthesize a metachromatic staining extracellular matrix indicative of a high proteoglycan content that is typical of the chondrocyte phenotype.

EXAMPLE 5

Matrices made by the process described in Example 1 comprising various ratios of collagen to polysaccharide are implanted into a full-thickness articular cartilage defect in the rabbit as described in Amiel et al., supra. Defects measuring approximately 3.7 mm in diameter and 5 mm deep defect are created in the center of the medial femoral condyles of adult male New Zealand white rabbits. The defects are then either filled with matrix or left unfilled as controls. The defects are evaluated morphologically and histologically at 6 and 12 weeks.

EXAMPLE 6

This example illustrates the effect of collagen and hyaluronate on fibrin coagulation.

The effect of collagen/hyaluronate gel on the coagulation time of fibrinogen was evaluated as follows: 0.5 ml of purified fibrinogen solution (30 mg/ml, PBS) was placed into a 10 ml glass tube and incubated in a water bath at 37° C. for 5 min. 0.1 ml of $CaCl_2$ solution (0.2 M) containing 0.5 NIH U of thrombin and various concentrations of collagen and hyaluronate-polyaldehyde were added and mixed with a stir bar. The time required for the formation of gel on top of the stir bar was recorded as the coagulation time. The results are shown in Table 1.

TABLE 1

Fibrin coagulation time in the presence of collagen and hyaluronate

| Sample | Collagen (mg/ml) | HA-pALD (mg/ml) | Coagulation time (sec.) |
| --- | --- | --- | --- |
| sample 1 | 0 | 0 | 44.3 +/− 2.5 |
| sample 2 | 9.0 | 0 | 55.6 +/− 1.2 |
| sample 3 | 4.5 | 10 | 26 +/− 2 |
| sample 4 | 3.6 | 8 | 26 |

* All tests were done in triplicate. Mean ± SD shown.

EXAMPLE 7

This example illustrates the three-dimensional scaffold formation of a crosslinked collagen-hyaluronate matrix comprising fibrinogen and thrombin in tissue culture medium.

This experiment was performed with a three-way stopcock equipped with male luer slip adapter, to which two syringes were connected. Syringe A contained 5 ml of fibrinogen and hyaluronate-polyaldehyde (20 mg/ml for each, in DMEM medium), syringe B contained thrombin (2 NIH U/ml, in DMEM medium) and collagen Semed S (Kensey Nash) suspension (20 mg/ml, in DMEM medium), which had been pre-blended to a fiber diameter of about 50 mm in a heavy duty blender. The contents of syringes were admixed quickly between the two syringes and the contents were drawn into one syringe which was then angled at 60° into a phosphate buffered saline (PBS) solution (40 ml in 100 ml glass beaker) and the contents were discharged into the PBS solution. The entire discharge including mixing was completed in 10 sec. No dissolution of the gel thus formed was observed after incubation at ambient temperature or at 37° C.

EXAMPLE 8

This example illustrates the three-dimensional scaffold formation of a crosslinked collagen-hyaluronate matrix comprising fibrinogen and thrombin in deionized water.

The experiment was performed with a three-way stopcock equipped with male luer slip adapter, to which two syringes were connected. Syringe A contained 5 ml of fibrinogen and hyaluronate-polyaldehyde (20 mg/ml for each, 12 mM NaOH), syringe B contained thrombin (2 NIH U/ml) and purified collagen solution (Collagen corporation, 3 mg/ml, 12 mM HCl). The contents of syringes were admixed quickly between the two syringes and the contents were drawn into one syringe which was then angled at 60° into a phosphate buffered saline (PBS) solution (40 ml in 100 ml glass beaker) and the contents were discharged into the PBS solution. The entire discharge was completed in 10 sec. No dissolution of the gel thus formed was observed after incubation at ambient temperature or at 37° C.

EXAMPLE 9

This example illustrates the evaluation of in vivo biocompatibility and residence time of a crosslinked collagen-hyaluronate matrix comprising fibrinogen and thrombin Gels with different compositions as described in Table 2 were prepared using a three-way stopcock equipped with male luer slip adapter, and two syringes. After mixing, the mixtures were cast in 24-well cell culture plate at the rate of 0.5 ml/well and allowed to stand at ambient temperature for 15 min. The gels thus formed were lyophilized, chopped to cubes 10×10×5 mm long, and sterilized with ethanol. These specimens were then placed in pouches made by blunt dissection in the tibial muscle of 4 to 5 week old male Sprague Dawley rats. The rats were sacrificed after 3, 7, and 14 days, and explants were evaluated histologically for biocompatibility and implant persistence.

TABLE 2

Compositions of matrices for in vivo test

| Sample | Fibrinogen (FN) (mg/ml) | Collagen (CN) (mg/ml) | HA-pALD (mg/ml) | Total Mass (mg/ml) | Thrombin (NIH U/ml) |
|---|---|---|---|---|---|
| FN | 40 | 0 | 0 | 40 | 2 |
| FN/HA-pALD | 36 | 0 | 4 | 40 | 2 |
| CN/HA-pALD | 0 | 36 | 4 | 40 | 2 |
| FN/CN | 20 | 20 | 0 | 40 | 2 |
| FN/CN/HA-pALD | 18 | 18 | 4 | 40 | 2 |
| CN | 0 | 40 | 0 | 40 | 2 |

Histologic evaluation showed an increased persistence of implants composed of collagen/hyaluronate and fibrin. At day 3, the majority of the implants comprising fibrin and fibrin/hyaluronate were digested. At day 7, all of fibrin-based matrices were completely resorbed, while a small amount of residual fibrin/hyaluronate matrix could still be observed. At day 14, only collagen-containing matrices could still be found at the implant sites. Starting at day 7, a few blood vessels could be observed in fibrin/collagen matrices and in fibrin/collagen/hyaluronate-polyaldehyde matrices, and also in the control, collagen matrices. In addition, compositions comprising hyaluronate appeared to enhance the growth of blood vessels.

What is claimed is:

1. A method for preparing a matrix to support the repair of tissue comprising the steps of oxidizing an exogenous polysaccharide to form a modified exogenous polysaccharide having aldehyde groups, reacting said modified exogenous polysaccharide with collagen under conditions whereby said aldehyde groups covalently react to crosslink with collagen to form said matrix and adding a growth factor to said matrix.

2. The method of claim 1 wherein said growth factor is selected from the group consisting of members of the TGF-β superfamily; members of the BMP family; the growth differentiation factors(GDF's); ADMP-1; members of the fibroblast growth factor family; members of the hedgehog family of proteins; members of the insulin-like growth factor (IGF) family; members of the platelet-derived growth factor (PDGF) family; members of the interleukin (IL) family; and members of the colony-stimulating factor (CSF) family.

3. The method of claim 2 wherein the growth factor is a bone morphogenic protein (BMP).

4. The method of claim 1 wherein the polysaccharide comprises hyaluronic acid, chondroitin sulfate, dermatan sulfate, keratan sulfate, heparan, heparan sulfate, dextran, dextran sulfate, or alginate.

5. The method according to claim 4, wherein said polysaccharide comprises hyaluronic acid.

6. The method according to claim 1 wherein the collagen is selected from the group consisting of Type 1 and Type II collagen.

7. The method according to claim 1, wherein said step of oxidizing said polysaccharide comprises treatment of said polysaccharide with periodate.

8. The method according to claim 1, wherein said collagen and said polysaccharide used to form said matrix are present in the range of 99:1 to 1:99 by weight, respectively.

9. The method according to claim 8 wherein said range is 9:1 to 1:9 by weight, respectively.

10. The method according to claim 1, wherein about 1% to 50% of the repeat units in said polysaccharide are oxidized to contain aldehyde groups.

11. The method according to claim 10, wherein about 1% to 5% of the repeat units in said polysaccharide are oxidized to contain aldehyde groups.

12. The method according to claim 1, wherein said matrix is formed by freezing and lyophilization.

13. The method according to claim 1, wherein said matrix is formed by wet laying and air drying.

14. The method of claim 1 further comprising adding fibrinogen and thrombin to form fibrin in said matrix.

15. The method of claim 1 wherein tissue is selected from the group consisting of bone, cartilage and soft tissue.

16. A matrix to support the repair of tissue, said matrix comprising a growth factor and collagen covalently crosslinked to an exogenous polysaccharide, wherein said polysaccharide is crosslinked to said collagen through oxidized sugar rings on said polysaccharide which form covalent linkages to said collagen.

17. The matrix of claim 16 wherein said growth factor is selected from the group consisting of members of the TGF-β superfamily; members of the bone morphogenic protein family; the growth differentiation factors(GDF's); ADMP-1; members of the fibroblast growth factor family; members of the hedgehog family of proteins; members of the insulin-like growth factor (IGF) family; members of the platelet-derived growth factor (PDGF) family; members of the interleukin (IL) family; and members of the colony-stimulating factor (CSF) family.

18. The matrix of claim 16 wherein said growth factor is a bone morphogenic protein.

19. The matrix according to claim 16 wherein said polysaccharide comprises hyaluronic acid, chondroitin sulfate, dermatan sulfate, keratan sulfate, heparan, heparan sulfate, dextran, dextran sulfate or alginate.

20. The matrix according to claim 19 wherein said polysaccharide is hyaluronic acid.

21. The matrix according to claim 16 wherein said matrix comprises said collagen and said polysaccharide in a weight ratio in the range of 99:1 to 1:99.

22. The matrix of claim 16 wherein said collagen is selected from the group consisting of Type 1 collagen and Type 2 collagen.

23. The matrix of claim 16 further comprising fibrin.

24. A method of conducting the growth of bone or cartilage tissue in vivo comprising the step of administering a matrix according to claim 16 at a site of desired bone growth.

* * * * *